US006841701B2

(12) United States Patent
Stürzebecher et al.

(10) Patent No.: US 6,841,701 B2
(45) Date of Patent: Jan. 11, 2005

(54) INHIBITORS FOR THE BLOOD-CLOTTING FACTOR XA

(75) Inventors: Jörg Stürzebecher, Erfurt (DE); Torsten Steinmetzer, Jena (DE); Sebastian Künzel, Jena (DE); Andrea Schweinitz, Jena (DE)

(73) Assignee: Curacyte AG, Munich (DE)

( * ) Notice: Subject to any disclaimer, the term of this patent is extended or adjusted under 35 U.S.C. 154(b) by 0 days.

(21) Appl. No.: 10/311,364

(22) PCT Filed: Jun. 15, 2001

(86) PCT No.: PCT/EP01/06814

§ 371 (c)(1),
(2), (4) Date: Mar. 21, 2003

(87) PCT Pub. No.: WO01/96366

PCT Pub. Date: Dec. 20, 2001

(65) Prior Publication Data

US 2003/0166577 A1 Sep. 4, 2003

(30) Foreign Application Priority Data

Jun. 15, 2000 (DE) ........................................ 100 29 015

(51) Int. Cl.$^7$ ........................ C07C 233/05; A61K 31/16
(52) U.S. Cl. .......................... 564/157; 564/32; 564/47; 564/56; 564/123; 564/152; 564/155; 514/588; 514/590; 514/616; 514/478; 560/24
(58) Field of Search ........................... 564/32, 47, 56, 564/123, 152, 157, 155; 514/588, 590, 616, 478, 646, 649; 560/29

(56) References Cited

U.S. PATENT DOCUMENTS

| 5,705,487 A | 1/1998 | Schacht et al. |
| 5,707,966 A | 1/1998 | Schacht et al. |
| 5,710,130 A | 1/1998 | Schacht et al. |
| 5,726,159 A | 3/1998 | Schacht et al. |
| 5,914,319 A | 6/1999 | Schacht et al. |

FOREIGN PATENT DOCUMENTS

| WO | WO 94/29336 | 12/1994 |
| WO | WO 95/29189 | 11/1995 |
| WO | WO 96/25426 | 8/1996 |
| WO | WO 00/58346 | 10/2000 |

OTHER PUBLICATIONS

CA:137:134463 abs of Bioorganic & Med Chem Letters by Kunzel et al 12(4) pp645–648 2002.*
CA:133:267159 abs of WO 2000058346 Oct. 5, 2000.*
Bookser et al., "Syntheses of Quadruply Two–and Three–Atom, Aza–Bridged, Cofacial Bis (5,10,15,20–Tetraphenylporphyrins)," *J. Am. Chem. Soc.* 113:4208–4218 (1991).
Gustafsson et al., "Effects of Inogatran, A New Low–Molecular–Weight Thrombin Inhibitor, in Rat Models of Venous and Arterial Thrombosis, Thrombolysis and Bleeding Time," *Blood Coagulation and Fibrinolysis* 7:69–79 (1996).

Hara et al., "DX–9065a, a New Synthetic, Potent Anticoagulant and Selective Inhibitor For Factor Xa," *Thrombosis and Haemostasis* 71:314–319 (1994).
Herbert et al., "DX 9065A, A Novel, Synthetic, Selective and Orally Active Inhibitor of Factor Xa: In Vitro and In Vivo Studies," *The Journal of Pharmacologically and Experimental Therapeutics* 276:1030–1038 (1996).
Ho et al., "Exploratory Solid–Phase Synthesis of Factor Xa Inhibitors: Discovery and Application of $P_3$–Heterocyclic Amides as Novel Types of Non–Basic Arginine Surrogates," *Bioorganic & Medicinal Chemistry Letters* 9:3459–3464 (1999).
Judkins et al., "A Versatile Synthesis of Amidines from Nitriles Via Amidoximes," *Synthetic Communications* 26:4351–4367 (1996).
Kettner et al., "The Selective Affinity Labeling of Factor $X_a$ By Peptides or Arginine Chloromethyl Ketone," *Thrombosis Research* 22:645–652 (1981).
Maduskuie et al., "Rational Design and Synthesis of Novel, Potent Bis–Phenylamidine Carboxylate Factor Xa Inhibitors," *J. Med. Chem.* 41:53–62 (1998).
Mohan et al., "Solid–Phase Synthesis of N–Substituted Amidinophenoxy Pyridines as Factor XA Inhibitors," *Bioorganic & Medicinal Chemistry Letters* 8:1877–1882 (1998).
Ostrem et al., "Discovery of a Novel, Potent, and Specific Family of Factor Xa Inhibitors via Combinatorial Chemistry," *Biochemistry* 37:1053–1059 (1998).
Phillips et al., "Discovery of N–[2–[5–[Amino(imino) Methyl]–2 Hydroxyphenoxy]–3,5–Difluoro–6–[3–(4, 5–Dihydro–1–Methyl–1H–Imidazol–2–yl) Phenoxy] Pyridin–4–yl]–N–Methylglycine (ZK–807834): A Potent, Selective, and Orally Active Inhibitor of the Blood Coagulation Enzyme Factor $Xa_1$," *J. Med. Chem.* 41:3557–3562 (1998).
Quan et al., "Bisbenzamidine Isoxazoline Derivatives as Factor Xa Inhibitors," *Bioorganic & Medicinal Chemistry Letters* 7:2813–2818 (1997).
Sato et al., "YM–60828, A Novel Factor Xa Inhibitor: Separation of its Antithrombotic Effects From its Prolongation of Bleeding Time," *European Journal of Pharmacology* 339:141–146 (1997).
Sato et al., "Antithrombotic Effects of YM–60828, a Newly Synthesized Factor Xa Inhibitor, in Rat Thrombosis Models and its Effects on Bleeding Time," *British Journal of Pharmacology* 123:92–96 (1998).

(List continued on next page.)

*Primary Examiner*—Shailendra Kumar
(74) *Attorney, Agent, or Firm*—Clark & Elbing LLP

(57) ABSTRACT

The invention relates to derivatives of amidinobenzylamine, especially derivatives of 4-amidinobenzylamine, with two bonded amino acids. These derivatives represent a novel group of highly active and very selective F Xa-inhibitors for treating cardiovascular diseases and thrombotic events.

7 Claims, No Drawings

OTHER PUBLICATIONS

Sperl et al., "Urethanyl–3–Amidinophenylalanine Derivatives as Inhibitors of Factor Xa. X–Ray Crytstal Structure of a Trypsin/Inhibitor Complex and Modeling Studies," *Biol. Chem.* 381:321–329 (2000).

Sturzebecher et al., "Synthetic Inhibitors of Bovine Factor Xa and Thrombin Comparison of Their Anticoagulant Efficiency," *Thrombosis Research* 54:245–252 (1989).

Tucker et al., "Potent Noncovalent Thrombin Inhibitors that Utilize the Unique Amino Acid D–Dicyclohexylalanine in the P3 Position. Implications on Oral Bioavailability and Antithrombotic Efficacy," *J. Med. Chem.* 40:1565–1569 (1997).

Wagner et al., "Synthese von N–[Amidinobenzyl]–und N–[Amidinophenyl]–Phthalimide und–1–Oxoisoindoline," *Pharmazie* 32:76–79 (1977).

* cited by examiner

INHIBITORS FOR THE BLOOD-CLOTTING FACTOR XA

CROSS-REFERENCE TO RELATED APPLICATIONS

The application is the National Stage of International Application No. PCT/EP01/06814, filed on Jun. 15, 2001, which claims benefit of DE 10029015.9, filed on Jun. 15, 2000.

The invention relates to novel inhibitors for the coagulation factor Xa for the treatment of cardiovascular diseases and for the prevention of thromboembolic events.

The anticoagulants of the heparin type or the vitamin K antagonists presently employed clinically do not comply with all requirements for an "ideal" antithrombotic. Therefore alternatives are sought with low molecular weight inhibitors of the coagulation enzymes, especially of thrombin and factor Xa (F Xa). A particular advantage of F Xa inhibitors in comparison with thrombin inhibitors could be the lower tendency to bleeding which has been shown in various animal experiments. Thus the bleeding time was only minimally influenced in antithrombotically effective doses (J. M. Herbert et al., J. Pharmacol. Exp. Ther. 276, 1030–1038, 1996; K. Sato et al., Brit. J. Pharmacol. 123, 92–96, 1998).

The first nonpeptide compounds having a high affinity for F Xa were symmetrical bisbenzamidines ($K_i$=13 nM for the most active compound BABCH) (J. Stürzebecher et al., Thromb. Res. 54, 245–252, 1998). The naphthamidine derivative DX-9065a has two basic groups and inhibits F Xa selectively with $K_i$=24 nM (T. Hara et al., Thromb. Haemost. 71, 314–319, 1994). The inhibitor YM-60828 (K. Sato et al., Eur. J. Pharmacol. 339, 141–146, 1997), which is structurally related to DX-9065a, is even more active ($K_i$=1.3 nM). In the meantime, a whole series of further bis-basic compounds have been described in which, for example, two benzamidine residues are linked via an oxazoline ring ($K_i$=18 nM) (M. L. Quan et al., Bioorg. Med. Chem. Lett. 7, 2813–2818, 1997) or a carboxymethyl-alkyl chain ($K_i$=34 nM) (T. P. Maduskuie et al., J. Med. Chem. 41, 53–62, 1998). The disadvantage of the bis-basic compounds is, in particular, the low bioavailability after oral administration.

Inhibitors for F Xa which only contain one basic group have also been described. N-substituted amidinophenoxypyridines ($K_i$=0.11 nM for BX-807834) were developed on the basis of BABCH (R. Mohan et al., Bioorg. Med. Chem. Lett. 8, 1877–1882, 1998; G. B. Phillips et al., J. Med. Chem. 41, 3557–3562, 1998). Amides of Nα-adamantyloxycarbonyl-3-amidinophenyl-alanine ($K_i$=74 nM for the most active compound) are selective inhibitors of F Xa (S. Sperl et al., Biol. Chem. 381, 321–329, 2000), while Nα-arylsulfonyl-aminoacylated esters of 3-amidinophenylalanine have a low inhibitory action ($K_i$≈840 nM for TAPAM) (J. Stürzebecher et al., Thromb. Res. 54, 245–252, 1998). WO 96/10022 discloses inhibitors which no longer have any strong charge at all ($K_i$=3.0 nM for the most active compound).

Until now, only a few peptides which are derived from the substrate sequence Ile-Glu-Gly-Arg have been described as inhibitors of F Xa. The chloromethyl ketones described by Kettner and Shaw (Thromb. Res. 22, 645–652, 1981) inhibit F Xa irreversibly and are not suitable for in vivo applications. On the other hand, the peptides SEL 2489 ($K_i$=25 nM) and SEL 2711 ($K_i$=3 nM) are extremely active (J. A. Ostrem et al., Biochemistry 37, 1053–1059, 1998). Some peptidyl arginine aldehydes have also been described which, in addition to argininal in the P1 position, have a D-arginine or an unnatural basic amino acid in P3 (Z. H. Jonathan, Bioorg. Med. Lett. 9, 3459–3464, 1999). However, so far no peptidyl agmatine derivatives are known as inhibitors of F Xa, although this type of inhibitor has led to considerable advances in the further development of thrombin inhibitors. In this case, the successes with compounds of the D-Phe-Pro-Arg type having a C-terminal agmatine and derivatives derived therefrom were particularly noteworthy. Picomolar $K_i$ values were achieved for thrombin inhibition and the oral bioavailability was improved (T. J. Tucker et al., J. Med. Chem. 40, 1565–1569 and 3687–3693, 1997). In this case, however, no inhibition of F Xa was observed. For instance, melagatran, which has a 4-amidinobenzylamine residue at the C terminus and is very unspecific, inhibits F Xa with a $K_i$=2.8 μM. On the other hand, trypsin ($K_i$=4.0 nM) and thrombin ($K_i$=2.0 nM) are inhibited more than three orders of magnitude more strongly (D. Gustafsson et al., Blood Coagul. Fibrinolysis 7, 69–79, 1996).

The invention is based on the object of specifying an active compound which is also suitable for therapeutic applications and inhibits the coagulation factor Xa with high activity and specificity and which can be prepared with the lowest possible synthesis expenditure.

Surprisingly, it has been found that acylated amidinobenzylamine according to the general formula I shown in Patent claim 1, in particular compounds of 4-amidinobenzylamine in which X, $R_1$, $R_2$ and $R_3$ result in natural and/or unnatural amino acids, inactivate factor Xa very efficaciously and selectively and effectively inhibit the coagulation of human blood plasma. Amidinobenzylamine in this case forms a particularly active inhibitor of factor Xa if the amidino group is in the 4-position, glycine and D-serine tert-butyl ether are bonded as amino acids and if the compound has an N-terminal protective group $R_4$ composed of an aryl- or aralkylsulfonyl residue.

Besides factor Xa, other enzymes were markedly less inhibited by the glycine derivatives, such that the derivatives of amidinobenzylamine according to the invention are a novel group of highly active and very selective F Xa inhibitors. In contrast to this, compounds which carry no H as $R_1$ (e.g. alanine derivatives) no longer selectively inhibit factor Xa, but are also strong inhibitors of trypsin, thrombin and plasmin.

The compounds are as a rule present as salts with mineral acids, preferably as hydrochlorides, or as salts with suitable organic acids.

The compounds of the general formula I can be prepared in a manner known in principle, as described below:

The starting compound 4-cyanobenzylamine is prepared from 4-cyanobenzyl bromide via Gabriel synthesis (G. Wagner and I. Wunderlich, Pharmazie 32, 76–77, 1977; B. C. Bookser and T. C. Bruice, J. Am. Chem. Soc. 113, 4208–4218, 1991). The Boc-protected acetyloxamidinobenzylamine is obtained from the 4-cyanobenzylamine thus prepared. The coupling of the further amino acids and of the protective group $R_4$ is carried out by means of standard coupling methods using Boc as an N-terminal protective group. The second amino acid can also be coupled directly as an N-aryl- or N-aralkylsulfonyl-protected amino acid. The peptide analogs are synthesized sequentially, beginning from the acetyloxamidinobenzylamine. Most of the products crystallize well and can thus be simply purified. The purification of the inhibitors is carried out in the last stage by means of preparative, reversed-phase HPLC.

The invention will be illustrated in greater detail below with the aid of three working examples:

WORKING EXAMPLE 1

Synthesis of benzylsulfonyl-D-Ser(Bz)-Gly-4-amidino-benzylamide×HCl

1.1 Boc-4-cyanobenzylamide 20 g (0.151 mol) of 4-cyanobenzylamine were dissolved in 300 ml of $H_2O$, 150 ml of dioxane and 150 ml of 1 N NaOH. 37.5 ml of di-tert-butyl dicarbonate were added dropwise with ice cooling and the mixture was stirred at 0° C. for one hour and at room temperature for a further 24 hrs. The dioxane was removed i.v. and the aqueous residue was extracted 3 times with ethyl acetate. The combined extracts were washed 3 times with 5% strength $KHSO_4$ solution and 3 times with saturated NaCl solution, dried over $Na_2SO_4$ and concentrated i.v. (white crystals). HPLC: acetonitrile/$H_2O$, elution in 44.1% acetonitrile; yield: 30.48 g (0.131 mol), 87%.

1.2 Boc-4-acetyloxamidinobenzylamide

According to Judkins et al. (Synthetic Comm. 26, 4351–4367, 1996), 30.48 g (0.131 mol) of Boc-4-cyanobenzylamide were dissolved in 300 ml of abs. ethanol with 13.65 g (0.197 mol) of hydroxylamine×HCl and 34 ml (0.197 mol) of DIEA. The solution was refluxed for 2 hrs and stirred at room temperature overnight. The batch was then concentrated i.v., the residue was dissolved in about 200 ml of acetic acid and the solution was treated with 18.67 ml (0.197 mol) of acetic anhydride. After 1 hr, it was again concentrated, dissolved in ethyl acetate and washed 3 times each with 5% strength $KHSO_4$ solution and saturated NaCl solution at 0° C. After drying over $Na_2SO_4$ and concentrating i.v., a white powder precipitated. HPLC: acetonitrile/$H_2O$, elution in 32.0% acetonitrile; yield: 31.3 g (0.102 mol) 78%.

1.3 4-acetyloxamidinobenzylamine×HCl 5 mmol of Boc-4-acetyloxamidinobenzylamide are dissolved in 20 ml of 1 N HCl in glacial acetic acid and the solution is allowed to stand at room temperature for 45 min. It is then largely concentrated i.v., and the product is precipitated using dry diethyl ether, filtered off on a frit, washed again with fresh ether and dried i.v. On account of the quantitative reaction, the product was employed for the next synthesis step without further purification.

1.4 Boc-Gly-4-acetyloxamidinobenzylamide

The coupling of Boc-Gly-OH (Orpegen, Heidelberg) to 4-acetyloxamidinobenzylamine was carried out according to Frérot et al. (Tetrahedron 47, 259 ff., 1991). To this end, 2.064 g (9.3 mmol) of 4-acetyloxamidinobenzylamine×HCl and 1.629 g (9.3 mmol) of Boc-Gly-OH were dissolved in about 25 ml of DMF. 4.84 g (9.3 mmol) of PyBOP and 3.878 ml (27.9 mmol) of TEA were then added at 0° C. and the pH was adjusted to 9 using TEA. After stirring at room temperature for 1 hr, the mixture was concentrated i.v., taken up in ethyl acetate and subjected to acidic, basic and neutral washing 3 times each, dried and concentrated. Yield: 3 g (8.2 mmol) 88%.

1.5 Boc-Gly-4-amidinobenzylamide×AcOH 3 g (8.2 mmol) of Boc-Gly-4-Acetyloxamidinobenzylamide were dissolved in 200 ml of 90% strength acetic acid. 300 mg of 10% palladium on activated carbon were then added under argon. Argon was replaced by a hydrogen atmosphere and the batch was hydrogenated for 24 hrs with vigorous stirring. The catalyst was filtered off and the filtrate was concentrated i.v. Yield: 2.9 g (7.9 mmol) 96%.

1.6 H-Gly-4-amidinobenzylamide×2 HCl 2.9 g (7.9 mmol) of Boc-Gly-4-amidinobenzylamide were dissolved in 100 ml of 1 N HCl in glacial acetic acid and the solution was allowed to stand at room temperature for 45 min. It was then largely concentrated i.v. and precipitated using dry diethyl ether, then filtered off on a frit and the product was again washed with fresh ether. After drying the product i.v., it was used without further purification for the synthesis according to item 1.8.

1.7 Benzylsulfonyl-D-Ser(Bz)-OH 229 mg (1.173 mmol) of H-D-Ser(Bz)-OH and 408 µl (2.345 mmol) of DIEA were dissolved in 50 ml of 50% acetonitrile. 335 mg (1.76 mmol) of benzylsulfonyl chloride were then added and the mixture was stirred at room temperature for 12 hrs. It was concentrated i.v., taken up using ethyl acetate and subjected to acidic and neutral washing 3 times each. After drying over sodium sulfate, it was concentrated i.v. Yield: 289 mg (0.827 mmol) 71%.

1.8 Benzylsulfonyl-D-Ser(Bz)-Gly-4-amidinobenzylamide×TFA 151 mg (0.433 mmol) of benzylsulfonyl-D-Ser(Bz)-OH and 121 mg (0.433 mmol) of H-Gly-4-amidinobenzylamide×2 HCl were dissolved in a little abs. DMF. 225 mg (0.433 mmol) of PyBOP and 230 µl (1.32 mmol) of DIEA were added with ice cooling. After stirring at room temperature for 1 hr, the mixture was concentrated i.v. and the product was purified by means of HPLC (acetonitrile/$H_2O$, 0.1% trifluoroacetic acid, elution in 37.4% acetonitrile). Yield: 232 mg (0.356 mmol) 82%.

WORKING EXAMPLE 2

Inhibition of F Xa by selected compounds having Y = amidino

| $R_4$ | $R_3$ configuration | $R_3$ | $R_2$ | $X-R_1$ | Amidino position | $K_b$ µM |
|---|---|---|---|---|---|---|
| H | L | $CH_2$—OH | H | $CH_2$ | 4 | >1000 |
| Boc | L | $CH_2$—OH | H | $CH_2$ | 4 | 110 |
| H | D | $CH_2$—OH | H | $CH_2$ | 4 | >1000 |
| Ac | D | $CH_2$—OH | H | $CH_2$ | 4 | >1000 |
| Bz—$SO_2$ | D | $CH_2$—OH | H | $CH_2$ | 4 | 3.0 |
| Bz—$SO_2$ | D | $CH_2$—O—Bz | H | $CH_2$ | 4 | 0.050 |
| Bz—$SO_2$ | D | $CH_2$—O—tBu | H | $CH_2$ | 4 | 0.030 |
| Bz—$SO_2$ | D | $CH_2$—O—tBu | H | $CH_2$—$CH_3$ | 4 | 0.044 |
| H | D | $CH_2$—O—Bz | H | $CH_2$ | 3 | 140 |
| Boc | D | $CH_2$—O—Bz | H | $CH_2$ | 3 | 93 |
| Bz—$SO_2$ | D | $CH_2$—O—Bz | H | $CH_2$ | 3 | 84 |

Determination of the Inhibitory Action

For the determination of the inhibitory action, 200 µl of tris buffer (0.05 M, 0.154 M NaCl, 5% ethanol, pH 8.0; contains the inhibitor), 25 µl of substrate (Moc-D-Nle-Gly-Arg-pNA in $H_2O$; Pentapharm Ltd., Basle, Switzerland) and 50 µl of F Xa (from Rind, Diagnostic Reagents Ltd, Thame, GB) were incubated at 25° C. After 3 min, the reaction was interrupted by addition of 25 µl of acetic acid (50%) and the absorption at 405 nm was determined by means of microplate reader (MR 5000, Dynatech, Denkendorf, Germany). The $K_i$ values were determined according to Dixon (Biochem. J. 55, 170–171, 1953) by linear regression by means of a computer program. The $K_i$ values are the mean of at least three determinations.

WORKING EXAMPLE 3

| Inhibition of the coagulation of human plasma by benzylsulfonyl-D-Ser(Bz)-Gly-4-amidinobenzylamide | | |
|---|---|---|
| Concentration | Prolongation of the coagulation time (%) | |
| μM | aPTT | PT |
| 3.3 | 385 | 386 |
| 1.7 | 260 | 266 |
| 0.83 | 185 | 198 |
| 0.42 | 146 | 153 |
| 0.21 | 122 | 127 |
| 0.1 | 111 | 119 |

Determination of the Inhibition of Coagulation

For the determination of the prothrombin time (PT), 100 μl of thromboplastin (Dade, Unterschleißheim) and 100 μl of inhibitor, dissolved in $CaCl_2$ (0.05 M, 5% ethanol) were incubated at 37° C. for 2 min and the coagulation was started by addition of 100 μl of human citrate plasma. For the determination of the activated partial thromboplastin time (aPTT), 100 μl of human citrate plasma were incubated with 100 μl of aPTT reagent (Roche Diagnostics, Mannheim) at 37° C. for 3 min and the coagulation was started by addition of 100 μl of inhibitor, dissolved in $CaCl_2$ (0.05 M, 5% ethanol). The coagulation times were determined using the Thrombotrack coagulometer (Immuno, Heidelberg).

| Abbreviations used: | |
|---|---|
| Ac | acetyl |
| Boc | tert-butyloxycarbonyl |
| Bz | benzyl |
| DIEA | diisopropylethylamine |
| DMF | N,N-dimethylformamide |
| i.v. | in vacuo |
| PyBOP | benzotriazol-l-yl-N-oxytris-(pyrrolidino) phosphonium hexafluorophosphate |
| TEA | triethylamine |
| TFA | trifluoroacetic acid |
| THF | tetrahydrofuran |
| tBu | tert-butyl |

What is claimed is:

1. Inhibitors for the coagulation factor Xa of the formula:

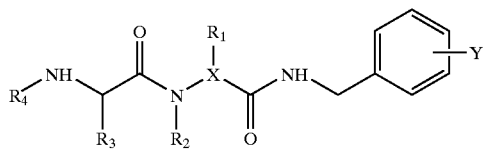

in which the substituent Y occurs in the 3- or 4-position and is an amidino group

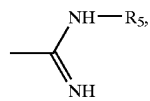

in which $R_5$ is selected from the group consisting of H, OH, —CO—$R_7$ and —COO—$R_7$, where $R_7$ is selected from a branched or unbranched alkyl having 1–16 C atoms, a substituted or unsubstituted aryl or heteroaryl group and a substituted or unsubstituted aralkyl or heteroaralkyl group, X is CH or N, $R_1$ is H or a branched or unbranched alkyl having 1–8 C atoms or $(CH_2)_n$—OH where n=1–5, $R_2$ is H or a branched or unbranched alkyl having 1–8 C atoms, $R_3$ is a branched or unbranched alkyl having 1–8 C atoms or $(CH_2)_n$—O—$R_6$, where N=1–5 and $R_6$ is a branched or unbranched alkyl having 1–6 C atoms, a substituted or unsubstituted aryl or heteroaryl group or a substituted or an unsubstituted aralkyl or heteroaralkyl group and $R_4$ is selected from the group consisting of —$SO_2$—$R_8$, —CO—$R_8$, —COO—$R_8$ and H, where $R_8$ is a branched or unbranched alkyl having 1–16 C atoms, a substituted or an unsubstituted aryl or heteroaryl group, a substituted or unsubstituted aralkyl or heteroaralkyl group, an adamantyl group, a camphoryl group or a cyclohexylmethyl group.

2. Inhibitors according to claim 1, wherein Y is in the 4-position, X is CH, $R_1$ and $R_2$ are H, $R_3$ is $(CH_2)_n$—O—$R_6$, where n is 1 and $R_6$ is t-butyl, wherein $R_3$ is in the D configuration, and $R_4$ is —$SO_2$—$R_8$, wherein $R_8$ is a substituted or unsubstituted aryl or aralkyl group.

3. A method of preventing or treating thromboembolic diseases comprising administering to a patient a factor Xa inhibitor of claim 1.

4. The method of claim 3, wherein the factor Xa inhibitor is in the form of a tablet, coated tablet, capsule, pellet, suppository, solution or patch.

5. Inhibitors for the coagulation factor Xa of the formula:

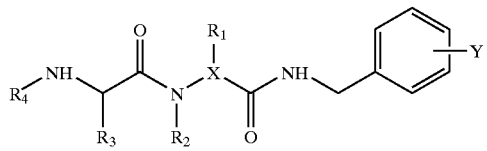

in which the substituent Y occurs in the 3- or 4-position and is an amidino group

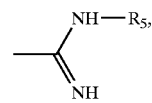

in which $R_5$ is selected from the group consisting of H, OH, —CO—$R_7$ and —COO—$R_7$, where $R_7$ is selected from a branched or unbranched alkyl having 1–16 C atoms, a substituted or unsubstituted aryl or heteroaryl group and a substituted or unsubstituted aralkyl or heteroaralkyl group, X is CH or N, $R_1$ is H or a branched or unbranched alkyl having 1–8 C atoms or $(CH_2)_n$—OH where n=1–5, $R_2$ is H or a branched or unbranched alkyl having 1–8 C atoms, $R_3$ is $(CH_2)_n$—S—$R_6$ or $(CH_2)_n$—NH—$R_6$ where n=1–5 and $R_6$ is a branched or unbranched alkyl having 1–16 C atoms, a substituted or unsubstituted aryl or heteroaryl group or a substituted or an unsubstituted aralkyl or heteroaralkyl group and $R_4$ is selected from the group consisting of —$SO_2$—$R_8$, —CO—$R_8$, —COO—$R_8$ and H, where $R_8$ is a branched or unbranched alkyl having 1–16 C atoms, a substituted or an unsubstituted aryl or heteroaryl group, a substituted or unsubstituted aralkyl or heteroaralkyl group, an adamantyl group, a camphoryl group or a cyclohexylmethyl group.

6. A method of preventing or treating thromboembolic diseases comprising administering to a patient a factor Xa inhibitor of claim 5.

7. The method of claim 6, wherein the factor Xa inhibitor is in the form of a tablet, coated tablet, capsule, pellet, suppository, solution or patch.

* * * * *

UNITED STATES PATENT AND TRADEMARK OFFICE
CERTIFICATE OF CORRECTION

PATENT NO. : 6,841,701 B2
DATED : January 11, 2005
INVENTOR(S) : Stürzebecher et al.

It is certified that error appears in the above-identified patent and that said Letters Patent is hereby corrected as shown below:

Column 5,
Line 60, replace " 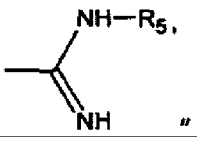 " with -- 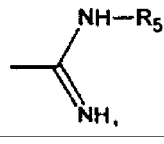 --.

Column 6,
Line 13, replace "1-6 C atoms" with -- 1-16 C atoms --.

Signed and Sealed this

Twelfth Day of July, 2005

JON W. DUDAS
*Director of the United States Patent and Trademark Office*